United States Patent

Failli et al.

[11] Patent Number: 5,164,399
[45] Date of Patent: Nov. 17, 1992

[54] RAPAMYCIN PYRAZOLES

[75] Inventors: Amedeo A. Failli, Princeton Junction, N.J.; Robert J. Steffan, Langhorne, Pa.

[73] Assignee: American Home Products Corporation, New York, N.Y.

[21] Appl. No.: 793,765

[22] Filed: Nov. 18, 1991

[51] Int. Cl.$^5$ ................. C07D 491/22; A61K 31/395
[52] U.S. Cl. .................................. 514/286; 540/456
[58] Field of Search ................... 540/456; 514/286

[56] References Cited

U.S. PATENT DOCUMENTS

| | | | |
|---|---|---|---|
| 3,929,992 | 12/1975 | Seghal et al. | 514/291 |
| 3,993,749 | 11/1976 | Seghal et al. | 514/291 |
| 4,316,885 | 2/1982 | Rakhit | 514/291 |
| 4,401,653 | 8/1983 | Eng | 514/291 |
| 4,650,803 | 3/1987 | Stella et al. | 514/291 |
| 4,885,171 | 12/1989 | Seghal et al. | 514/291 |
| 5,023,263 | 6/1991 | Caufield et al. | 514/291 |
| 5,078,999 | 1/1992 | Warner et al. | 215/291 |
| 5,080,899 | 7/1992 | Sturm et al. | 514/291 |

FOREIGN PATENT DOCUMENTS 0401747  12/1990  European Pat. Off. ............ 514/291

OTHER PUBLICATIONS

J. Antibiot. 28, 721 (1975).
J. Antibiot. 28, 727 (1975).
J. Antibiot. 31, 539 (1978).
Can. J. Physiol. Pharmacol. 55, 48 (1977).
FASEB 3, 3411 (1989).
FASEB 3, 5256 (1989).
Lancet 1183 (1978).
Med. Sci. Res. 17:877 (1989).

*Primary Examiner*—Robert T. Bond
*Attorney, Agent, or Firm*—Arnold S. Milowsky

[57] ABSTRACT

A compound of the structure

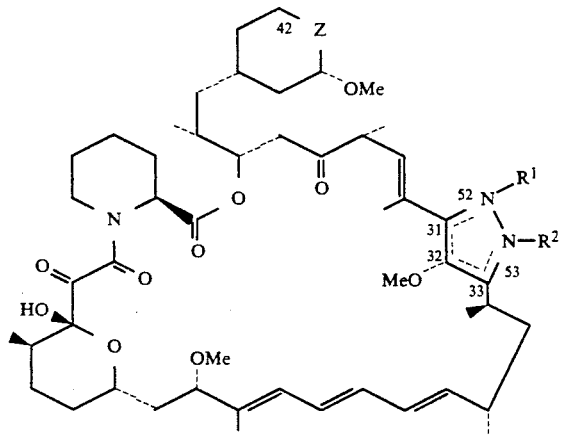

wherein Z is

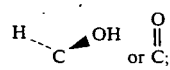

and $R^1$ is hydrogen, alkyl, or arylalkyl, provided that when $R^2$ is present, $R^1$ is absent;
$R^2$ is hydrogen, alkyl, or arylalkyl, provided that when $R^1$ is present, $R^2$ is absent;
the dotted lines in the pyrazole ring represent double bonds between the 31- and 32-positions and between the 33- and 53-positions when $R^1$ is present and double bonds between the 31- and 52-positions and between the 32- and 33-positions when $R^2$ is present;
or a pharmaceutically acceptable salt thereof which by virtue of its immunosuppressive activity is useful in treating transplantation rejection, host vs. graft disease, autoimmune diseases, and diseases of inflammation, by virtue of its antifungal activity is useful in treating fungal infections; and by virtue of its antitumor activity is useful in treating tumors. Intermediates possessing a 31,33-β-dicarbonyl moiety that are useful for the same purposes are also described.

7 Claims, No Drawings

RAPAMYCIN PYRAZOLES

BACKGROUND OF THE INVENTION

This invention relates to pyrazoles of rapamycin and intermediates thereof and a method for using them in the treatment of transplantation rejection, host vs. graft disease, autoimmune diseases, diseases of inflammation, tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). The ability of rapamycin to prolong survival time of organ grafts in histoincompatible rodents was disclosed by Morris [Med. Sci. Res. 17: 877 (1989)]. Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, antitumor, and antifungal agents having the structure

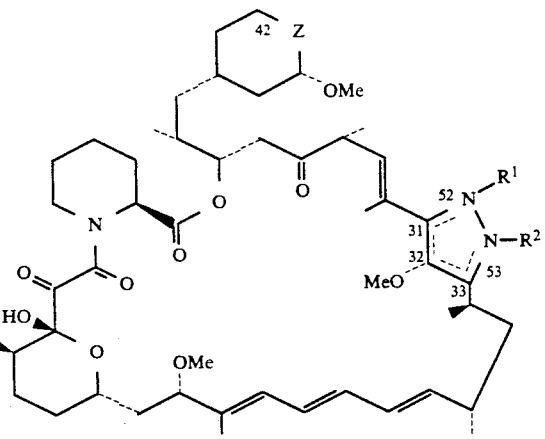

wherein Z is

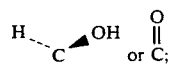

and
$R^1$ is hydrogen, alkyl of 1–6 carbon atoms, or arylalkyl of 7–10 carbon atoms, provided that when $R^2$ is present, $R^1$ is absent;
$R^2$ is hydrogen, alkyl of 1–6 carbon atoms, or arylalkyl of 7–10 carbon atoms, provided that when $R^1$ is present, $R^2$ is absent;
the dotted lines in the pyrazole ring represent double bonds between the 31- and 32-positions and between the 33- and 53-positions when $R^1$ is present and double bonds between the 31- and 52-positions and between the 32- and 33-positions when $R^2$ is present;
or a pharmaceutically acceptable salt thereof.

Of the compounds, preferred members are those in which Z is

It is preferred that the aryl portion of the arylalkyl substituent is a phenyl group that is optionally mono-, di-, or tri-substituted with a substituent selected from the group consisting of alkyl of 1–6 carbon atoms, alkoxy of 1–6 carbon atoms, hydroxy, cyano, halo, nitro, carbalkoxy of 2–7 carbon atoms, trifluoromethyl, amino, and carboxy.

The pharmaceutically acceptable salts may be formed from inorganic cations such as sodium, potassium, and the like; mono-, di-, and trialkyl amines of 1–6 carbon atoms, per alkyl group and mono-, di-, and trihydroxy-alkyl amines of 1–6 carbon atoms per alkyl group; and organic acids such as acetic, lactic, citric, tartaric, succinic, maleic, malonic, gluconic, and the like.

The compounds of this invention can be prepared by oxidizing rapamycin with a periodinane oxidizing reagent such as, Dess-Martin preiodinane [J. Org. Chem. 48: 4155 (1983)], to selectively provide either 31-oxorapamycin or 31,42-dioxorapamycin, as shown below.

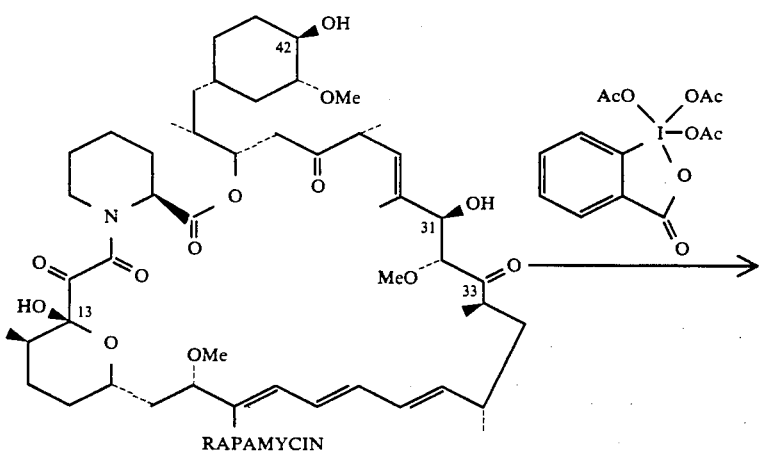

RAPAMYCIN

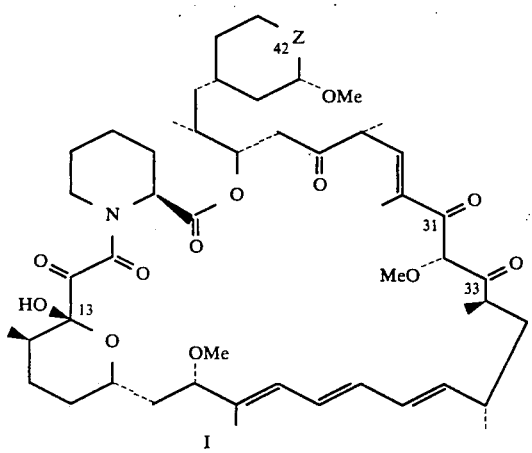

I

Although oxidation of a secondary alcohol to a ketone can be accomplished by numerous methods that have been described in the literature, selective oxidation of any of the hydroxy functions in polyhydroxylated macrocycles is by no means a trivial undertaking, since in such systems functional group reactivity cannot be readily predicted. [R. B. Woodward et al., J. Am. Chem. Soc. 103, 3215 (1981)]. Additionally, the oxidation of the hydroxyl functions of rapamycin was particularly difficult to achieve, since this polyfunctional macrocyclic lactone is sensitive to many of the conditions and reagents (particularly those containing chromium) which are routinely employed to oxidize other, less sensitive substrates. A method of making 42-oxorapamycin was disclosed in U.S. Pat. No. 5,023,263 using a rhuthenium oxidant; however, the selective oxidation of the 31-position of rapamycin over the oxidation of the 42-position was particularly unexpected in light of U.S. Pat. No. 5,023,263 which teaches the selective oxidation of the 42-position of rapamycin.

For the compounds of this invention in which the 42-position has not been oxidized, the pyrazole compounds of this invention can be made from the 31,33-$\beta$-dicarbonyl moiety by treatment with hydrazine, to provide a mixture of tautomers as shown below.

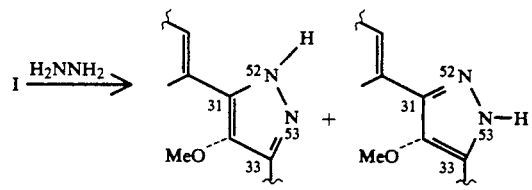

Substitution of the pyrazole ring to provide compounds in which $R^1$ or $R^2$ is other than hydrogen, can be accomplished by reacting the mixture of tautomeric pyrazole adducts with an alkylating agent, such as an alkyl halide in the presence of an acid scavenger, such as triethylamine or solid potassium carbonate, to provide a mixture of regioisomers that can be separated by conventional methods such as preparative high performance liquid chromatography. [see for example, Pyrazoles, Pyrazolines, Pyrazolidines, Indazoles and Condensed Rings, Wiley ed, 71 (1967)].

For the compounds of this invention in which the 42-position has been oxidized to a ketone, the pyrazole ring is made by first reacting the 31,33-$\beta$-dicarbonyl with hydrazine providing the above described pyrazole adduct followed by oxidation of the 42-hydroxyl group with Dess-Martin periodinane or a ruthenium based oxidizing agent. The oxidation step can be carried out either before or after alkylation of the pyrazole nitrogen for compounds in which $R^1$ or $R^2$ is other than hydrogen.

The reagents used to prepare the compounds of the invention are commercially available or can be prepared by methods that are disclosed in the literature.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed as the $IC_{50}$, expressed in nM, or as the percent inhibition at 100 nM.

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, i.p. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{{}^3H\text{-}PLN \text{ cells control } C3H \text{ mouse} - {}^3H\text{-}PLN \text{ cells rapamycin-treated } C3H \text{ mouse}}{{}^3H\text{-}PLN \text{ cells control } C3H \text{ mouse} - {}^3H\text{-}PLN \text{ cells test compound-treated } C3H \text{ mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28: 385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of a representative compound of this invention (Example 3) and the two 31,33-β-dicarbonyl intermediates (Examples 1 and 2) in these three standard test procedures.

TABLE 1*

| Compound | LAF $IC_{50}$ (nM) | LAF (100 nM)+ | PLN (ratio) | Skin Graft (days ± SD) |
|---|---|---|---|---|
| Example 1 | 84.9++ | 41 | ** | 9.16 ± 0.47 |
| Example 2 |  | 4 | ** | ** |
| Example 3 | 205.3++ |  | 0.52 | ** |
| Rapamycin |  | 94 |  | 11.66 ± 0.47 |

*Calculation of the PLN ratio was described supra.
**Not evaluated.
+Percent inhibition at 100 nM.
++Rapamycin had an $IC_{50}$ of 0.2 nM as a control for Example 1 and an $IC_{50}$ of 8.7 nM as a control for Example 3.

The results of these standard pharmacological test procedures demonstrate immunosuppressive activity both in vitro and in vivo for the pyrazoles of this invention and the intermediates thereof. Positive ratios in the LAF and PLN test procedures indicate suppression of T cell proliferation. As a transplanted pinch skin grafts are typically rejected within 6–7 days without the use of an immunosuppressive agent, the increased survival time of the skin graft when treated with the compounds of this invention further demonstrates their utility as immunosuppressive agents.

Based on the results of these standard pharmacological test procedures, the compounds of this invention are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease. Because the compounds and their intermediates are structurally related to rapamycin and have a similar immunosuppressive activity profile to rapamycin, the compounds of this invention and the intermediates thereof are considered to have antitumor and antifungal activities.

The compounds of this invention may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered topically.

The following examples illustrate the preparation of a representative compounds of this invention.

EXAMPLE 1

31-Deoxy-31-oxorapamycin

Under anhydrous conditions, a solution of rapamycin (2 g, 2.1 mmole) in 20 mL of dry dichloromethane, is treated with Dess-Martin periodinane (1.06 g, 2.5 mmole) in one portion. The reaction mixture was stirred at room temperature for 2 hours, diluted with dichloromethane and washed with saturated sodium bicarbonate and brine. After drying over $Na_2SO_4$, the solvent is removed in vacuo to yield a yellow foam. Purification by flash chromatography (on silica Merck 60, eluant: hexane-ethyl acetate 1:1) provided 0.650 g of the title compound as a pale yellow solid, which exists as a mixture of tautomers, as determined by HPLC (column: Altex Spherogel TSK 7.5 mm*60 cm; gradient elution, ethyl acetate in hexane 30 to 70%, flow rate: 5 mL/min).

$^1$H NMR ($CDCl_3$, 400 MHz): 1.642 and 1.655 (2s, 3H, $CH_3C{=}C$), 1.79–1.82 (m, 3H, $CH_3C{=}C$), 3.11–3.14 (m, 3H, $CH_3O$), 3.31–3.38 (m, 3H, $CH_3O$), 3.410–3.411 (2s, 3H, $CH_3O$).

$^{13}$C NMR ($CDCl_3$, 400 MHz): 210.8, 209.11, 207.95, 207.61, 207.17, 206.25, 202.089, 98.69, 98.65, 98.59, 97.55, 73.84.

MS (neg. ion FAB, m/z): 911 (M)$^-$, 880 (M—H—$OCH_3$)$^-$

EXAMPLE 2

31,42-Dideoxy-31,42-dioxorapamycin

The title compound was obtained as a minor product in the preparation of 31-deoxy-31-oxo rapamycin of Example 1. It was also determined to be a mixture of tautomers by the method described in Example 1.

$^1$H NMR ($CDCl_3$, 400 MHz): δ1.64 (s, 3H, $CH_3C{=}C$), 1.80 and 1.863 (2s, 3H, $CH_3C{=}C$), 3.123 (s, 3H, $CH_3O$), 3.33 and 3.36 (s, 3H, $CH_3O$), 3.461 (s, 3H, $CH_3O$).

MS (neg. ion FAB, m/z): 909 (M)$^-$, 878 (M—H—$OCH_3$)$^-$

Anal. Calc'd for $C_{51}H_{75}NO_{13}+3H_2O$: C, 63.53; H, 8.47; N, 1.45; Found: C, 63.60; H, 7.90; N, 1.36.

EXAMPLE 3

33-Deoxo-31-deoxy-31,33-(1-hydrazinyl-2-ylidene)-rapamycin

A solution of 31-deoxy-31-oxo Rapamycin of Example 1 (0.50 g, 0.55 mmole) and 85% hydrazine hydrate (0.033 g, 0.55 mmole) in 2 mL of methanol was heated with stirring at 60° C. for 2 hours. The solvent was removed in vacuo and the residue was purified by flash chromatography (on silica Merck 60, eluant: ethyl acetate-hexane 2:1) to provide 0.080 g of the title compound as a yellow solid.

$^1$H NMR ($CDCl_3$, 400 MHz): δ1.59 (s, 3H, $CH_3C{=}C$), 1.62 (2s, 3H, $CH_3C{=}C$), 3.11–3.25 (m, 3H, $CH_3O$), 3.36–3.42 (m, 3H, $CH_3O$), 3.61–3.68 (2s, 3H, $CH_3O$).

$^{13}$C NMR ($CDCl_3$, 400 MHz): δ208, 197, 170, 169.9, 169.28, 98.9, 98.6, 98.4, 84.94, 84.36.

MS (neg. ion FAB, m/z): 907 (M)⁻

What is claimed is:

1. A compound of the formula

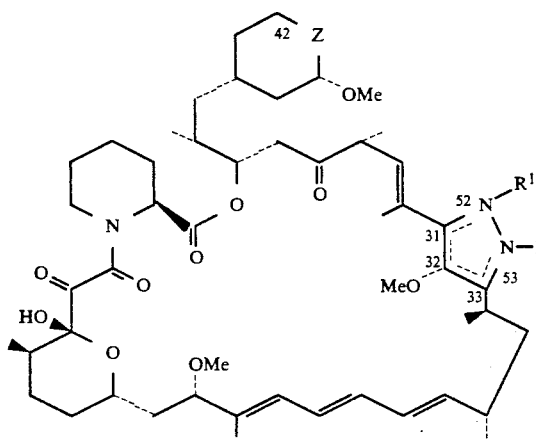

wherein
Z is

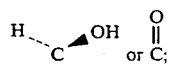

and

R¹ is hydrogen, alkyl of 1-6 carbon atoms, or phenylalkyl of 7-10 carbon atoms, provided that when R² is present, R¹ is absent; wherein the phenyl moiety of the phenylalkyl group is optionally mono-, di-, or tri-substituted with a substituent selected from the group consisting of alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

R² is hydrogen, alkyl of 1-6 carbon atoms, or phenylalkyl of 7-10 carbon atoms, provided that when R¹ is present, R² is absent; wherein the phenyl moiety of the phenylalkyl group is optionally mono-, di-, or tri-substituted with a substituent selected from the group consisting of alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

the dotted lines in the pyrazole ring represent double bonds between the 31- and 32-positions and between the 33- and 53-positions when R¹ is present and double bonds between the 31- and 52-positions and between the 32- and 33-positions when R² is present;

or a pharmaceutically acceptable salt thereof.

2. A compound of claim 1 wherein Z is

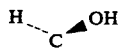

or a pharmaceutically acceptable salt thereof.

3. A compound of claim 1 which is 33-deoxo-31-deoxy-31,33-(1-hydrazinyl-2-ylidene) rapamycin or a pharmaceutically acceptable salt thereof.

4. 31-Deoxy-31-oxorapamycin or a pharmaceutically acceptable salt thereof.

5. 31,42-Dideoxy-31,42-dioxorapamycin or a pharmaceutically acceptable salt thereof.

6. A method of treating transplantation rejection, host vs. graft disease, autoimmune diseases, and diseases of inflammation in a mammal by administering to said mammal an immunosuppressive amount of a compound having the formula

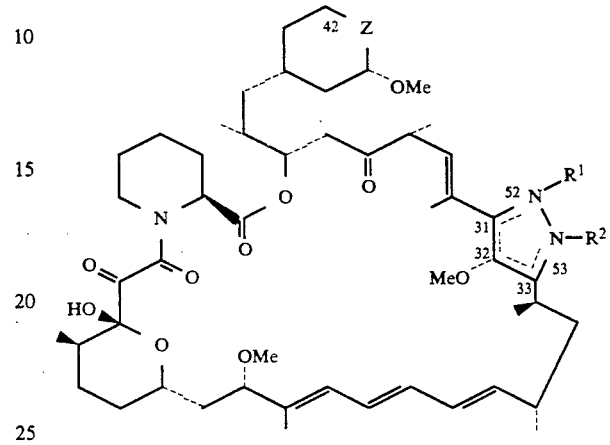

wherein
Z is

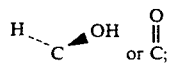

and

R¹ is hydrogen, alkyl of 1-6 carbon atoms, or phenylalkyl of 7-10 carbon atoms, provided that when R² is present, R¹ is absent; wherein the phenyl moiety of the phenylalkyl group is optionally mono-, di-, or tri-substituted with a substituent selected from the group consisting of alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

R² is hydrogen, alkyl of 1-6 carbon atoms, or phenylalkyl of 7-10 carbon atoms, provided that when R¹ is present, R² is absent; wherein the phenyl moiety of the phenylalkyl group is optionally mono-, di-, or tri-substituted with a substituent selected from the group consisting of alkyl of 1-6 carbon atoms, alkoxy of 1-6 carbon atoms, hydroxy, cyano, halo, nitro, carbalkoxy of 2-7 carbon atoms, trifluoromethyl, amino, and —CO₂H;

the dotted lines in the pyrazole ring represent double bonds between the 31- and 32-positions and between the 33- and 53-positions when R¹ is present and double bonds between the 31- and 52-positions and between the 32- and 33-positions when R² is present;

or a pharmaceutically acceptable salt thereof.

7. A pharmaceutical composition comprising an immunosuppressive amount of a compound having the formula

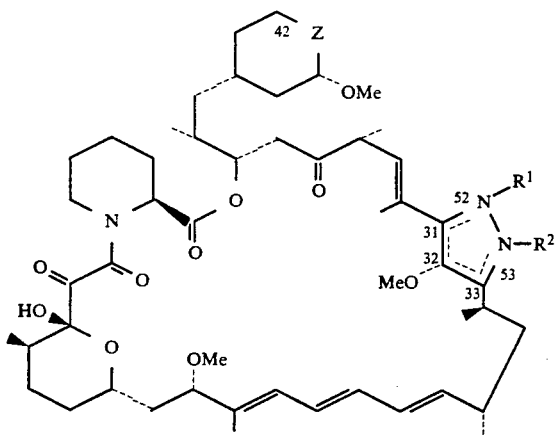

wherein Z is

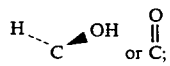

and

R[1] is hydrogen, alkyl of 1-6 carbon atoms, or phenylalkyl of 7-10 carbon atoms, provided that when R[2] is present, R[1] is absent; wherein the phenyl moiety of the phenylalkyl group is optionally mono-, di-, or tri-substituted with a substituent selected from the group consisting of alkyl of 1-6 carbon atoms, alkoxy of 1-6 carbon atoms, hydroxy, cyano, halo, nitro, carbalkoxy of 2-7 carbon atoms, trifluoromethyl, amino, and —$CO_2H$;

R[2] is hydrogen, alkyl of 1-6 carbon atoms, or phenylalkyl of 7-10 carbon atoms, provided that when R[1] is present, R[2] is absent; wherein the phenyl moiety of the phenylalkyl group is optionally mono-, di-, or tri-substituted with a substituent selected from the group consisting of alkyl of 1-6 carbon atoms, alkoxy of 1-6 carbon atoms, hydroxy, cyano, halo, nitro, carbalkoxy of 2-7 carbon atoms, trifluoromethyl, amino, and —$CO_2H$;

the dotted lines in the pyrazole ring represent double bonds between the 31- and 32-positions and between the 33- and 53-positions when R[1] is present and double bonds between the 31- and 52-positions and between the 32- and 33-positions when R[2] is present;

or a pharmaceutically acceptable salt thereof and a pharmaceutical carrier.

* * * * *